United States Patent [19]

Hughes

[11] 4,024,530
[45] May 17, 1977

[54] BACTERIA IDENTIFICATION DEVICE

[76] Inventor: Arleigh Bruce Hughes, 158 Haulani St., Pukalani, Hawaii

[22] Filed: Dec. 23, 1975

[21] Appl. No.: 643,852

[52] U.S. Cl. .............................. 340/332; 23/230 B; 128/2.05 R; 195/103.5 R; 340/286; 340/336; 340/365 S

[51] Int. Cl.$^2$ .......................................... G08B 5/36

[58] Field of Search .......... 340/286, 332, 323, 336; 128/2.05 R; 23/230 B; 195/103.5 R

[56] References Cited

UNITED STATES PATENTS

| | | | |
|---|---|---|---|
| 2,081,822 | 5/1937 | Kimbell | 340/323 |
| 2,254,619 | 9/1941 | Meyer | 340/323 |
| 2,614,840 | 10/1952 | Monkres | 340/323 X |
| 3,307,148 | 2/1967 | Fukamachi | 340/332 X |
| 3,548,806 | 12/1970 | Fisher | 128/2.05 R |
| 3,814,082 | 6/1974 | Taylor | 128/2.05 R |
| 3,832,288 | 8/1974 | Rollender et al. | 195/103.5 R |
| 3,895,807 | 7/1975 | Friedman | 340/323 X |
| 3,914,758 | 10/1975 | Ingle | 340/336 |
| 3,936,356 | 2/1976 | Janin | 195/103.5 R |
| 3,957,586 | 5/1976 | Babson et al. | 195/103.5 R |

OTHER PUBLICATIONS

Shayegani, et al.; "Evaluation of the Enteric Analyzer for Identification of Enterobacteriaceae"; *Journal of Clinical Microbiology*; Sept. 1975; pp. 186–192.

Brenner, et al.; "Evaluation of the Enteric Analyzer, An Instrument to Aid in the Identification of Enterobacteriaceae"; *Journal of Clinical Microbiology*; Sept. 1975; pp. 235–242.

Primary Examiner—David L. Trafton
Attorney, Agent, or Firm—Littlepage, Quaintance, Murphy

[57] ABSTRACT

A seven-segment display provides a set of eight lamps for each category of a test sample (such as bacteria) to be identified by the device. Manually operated electrical switches are used to enter and store the results of a plurality of tests (such as biological tests) into the device. Logic circuitry responds to the positions of the switch to control the lighting of individual lamps in the sets for the categories which have a significant positive correlation to the results entered by the switches. The display for which the greatest number of lamps in the most significant positions are lighted represents the category of the test sample being tested.

4 Claims, 5 Drawing Figures

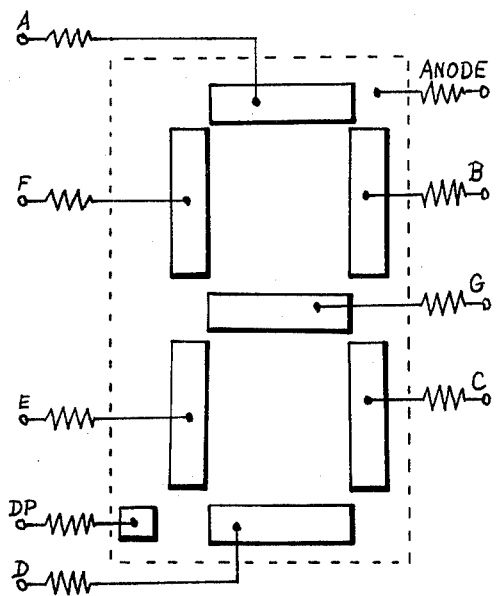
Fig. 3
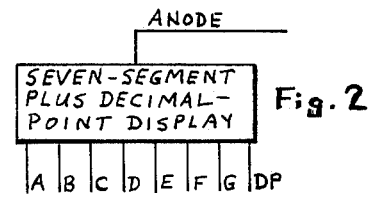
Fig. 2
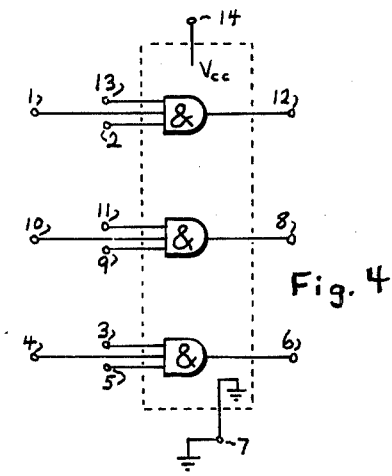
Fig. 4
Fig. 5

BACTERIA IDENTIFICATION DEVICE

BACKGROUND OF THE INVENTION

1. Field of the Invention

The invention relates to a data processing device for evaluating the results of a number of bacteria-identification tests to determine what type of bacteria is being tested.

2. Description of the Prior Art

Bacteria belong to a number of genera. There may be a large number of species within a genus. In general, the bacteria in any one genus give a predetermined positive or negative result to certain laboratory tests. These tests are therfore used in combination to determine the genus of any unknown bacteria which is presented to a biological laboratory for examination. One difficulty with such tests is that unusual species of a genus may give test results which are abnormal for that genus. For this reason, the results of a single test frequently cannot be used to provide a conclusive discrimination between two genuses.

Computers have previously been programmed to analyze test results for identification of bacteria, but the complexity and expense of such computers have prevented their widespread use. U.S. Pat. No. 2,352,182 discloses a simple switch-operated teaching device for identifying orders of the animal kingdom, but is useless in a test sequence in which individual tests are not conclusive, but only indicate probabilities.

SUMMARY OF THE INVENTION

In order to indicate probabilities that a test sample falls into one of a plurality of categories or genuses, a set of indicators is provided for each category. While any set of lamps could be used as this set of indicators, in the preferred embodiment, a light-emitting diode (LED) numerical display provides the set of lamps. These LED displays are commonly called seven-segment displays, although an eighth segment is usually provided as the decimal point. Because seven-segment displays are mass-produced and widely used, they enable a device according to the invention to be produced more cheaply than if seven or eight individual lamps were provided for each category.

Also, a switch means is provided for each test to be run, by means of which an electrical connection is made corresponding to the test result. Logic circuitry connects the switch means and the LED's to light the proper LED's when the switches are thrown.

The various lamps in a set have a hierarchy of importance. For example, using a seven-segment display, the test connected to the most significant A segment will usually be consistently accurate for 99% or more of the species of the genus corresponding to the displayed segment. The test connected to the least significant G or decimal point (DP) segments may be accurate for only 70 to 80% of the species or strains.

Thus, the user of a device according to the invention, after conducting a series of tests, can evaluate the tests by operating the switches to correspond to the results of the tests and can then observe the test evaluation made by the device by observing which set of lamps is most fully lighted, keeping in mind which lamps are most significant.

By appropriate connection of the logic circuitry, various test-evaluation algorithms can be mechanized. Although the preferred embodiment uses hard-wired logic, a device could be constructed using some form of programmable wiring, perhaps a simple plug-and-socket arrangement. Alternatively, a separate printed-circuit board could embody all logic connections and be interchangeable with other such boards at will. While the preferred embodiment of the invention is used for bacteria identification, the device might be used for other purposes.

BRIEF DESCRIPTION OF THE DRAWINGS

FIG. 2 is a block diagram showing the connections made to a conventional seven-segment display block as used in the embodiment of FIG. 1.

FIG. 3 is a diagram of a conventional seven-segment display, showing which terminal connections control which display segments.

FIG. 4 is a block diagram of a conventional three-AND-gate integrated circuit unit used in the embodiment of FIG. 1.

FIG. 5 is a circuit diagram of a modification of the device for indicating probabilities in cases where the indication provided by FIG. 1 is ambiguous.

DESCRIPTION OF THE PREFERRED EMBODIMENTS

Figure 1:
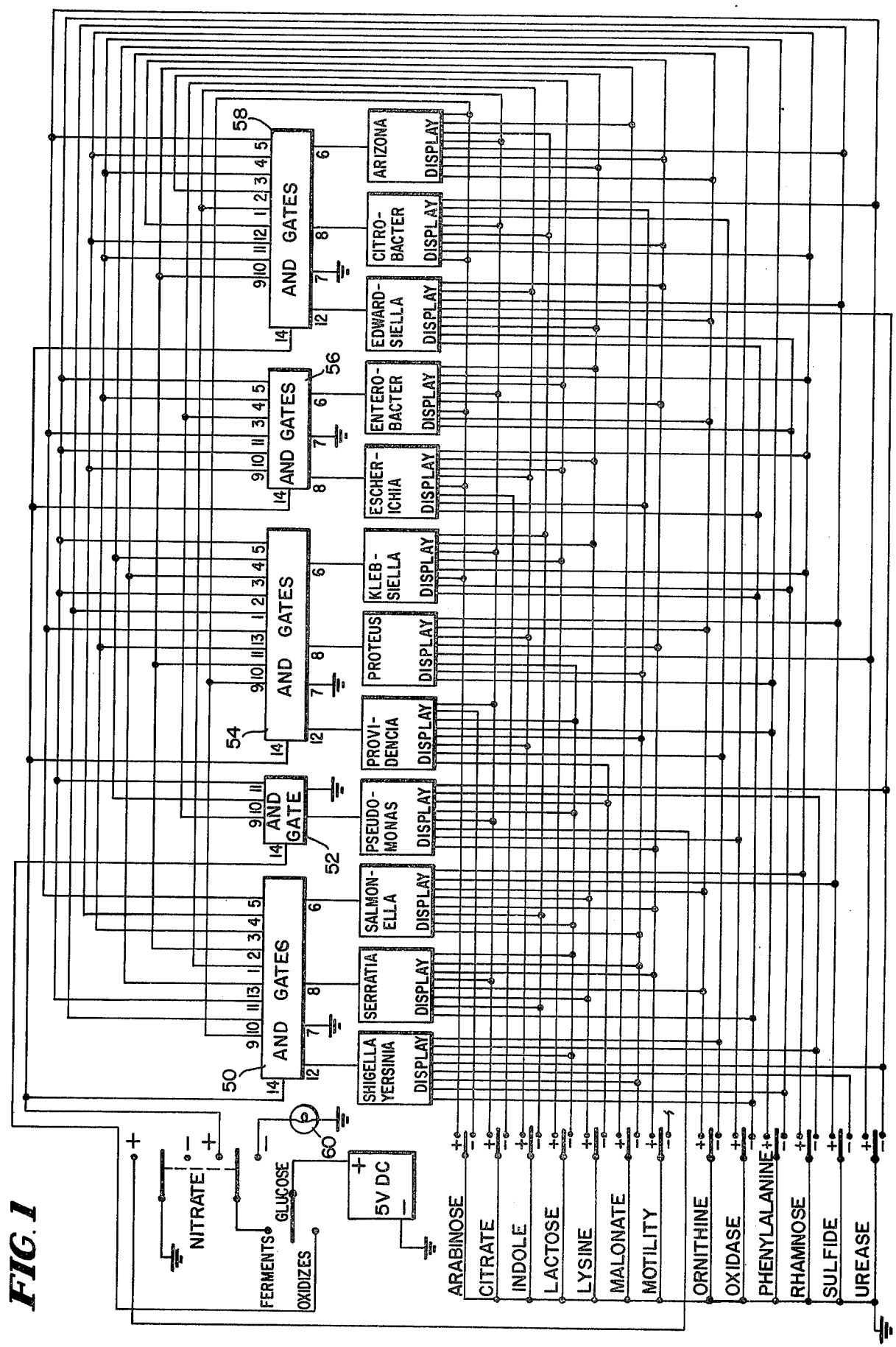
FIG. 1 is an overall block diagram of a preferred embodiment of the invention.

FIG. 1 is an overall diagram of a device according to the invention for use in identifying gram negative bacilli, especially those which ferment glucose and reduce nitrate. This has been called model A of the device, so that the logic embodied in FIG. 1 is also given in tabular form in Table 1 attached to this specification. Four other tables are also given, corresponding to other embodiments of the device, which are not otherwise illustrated.

In FIG. 1, 15 input switches are provided for indicating the results of tests corresponding to their labels. The 15 switches are respectively labelled: ARABINOSE, CITRATE, INDOLE, LACTOSE, LYSINE, MALONATE, MOTILITY, ORNITHINE, OXIDASE, PHENYLALANINE, RHAMNOSE, SULFIDE, UREASE, NITRATE and GLUCOSE, each switch label corresponding to a well-known bacteria identification test. The first-named 14 switches are switched between positive and negative positions to indicate whether the test results of those tests were positive or negative, as such test results are defined in the bacterial testing art. The 15th switch, GLUCOSE, is switched between one position (FERMENTS) which indicates that the bacteria being tested ferments glucose and a second position (OXIDIZES) which indicates that the bacteria oxidizes glucose.

Twelve seven-segment (plus decimal point) displays are provided and are respectively labelled SHIGELLA/YERSINIA, SERRATIA, SALMONELLA, PSEUDOMONAS, PROVIDENCIA, PROTEUS, KLEBSIELLA, ESCHERICHIA, ENTEROBACTER, EDWARDSIELLA, CITROBACTER and ARIZONA, corresponding to the genus of the bacteria represented by the respective display. FIG. 2 is a block diagram of the connections to a typical commercially available seven segment display which represents the arrangement of the inputs to the 12 displays used in FIG. 1. FIG. 3 represents the connections of the inputs to FIG. 2 to a seven-segment display.

Twelve AND gates provide the logic for controlling the 12 seven-segment displays. In the embodiment illustrated in FIG. 1, these AND gates are embodied in five integrated circuits 50, 52, 54, 56 and 58, which may be of the type illustrated in FIG. 4, with connections as identified on the individual circuits and in FIG. 4.

Table 1 and FIG. 1 represent the same device. In the SHIGELLA/YERSINIA the letter indicates the segment of the LED which is grounded by a particular switch. For example, the A segment of the ARIZONA display is grounded by the positive position of the ORNITHINE switch. The ORNITHINE switch also grounds the D segment of the EDWARDSIELLA and SERRATIA displays and three other displays when in the positive position. A minus test result on the ORNITHINE switch will ground the F segment of the CITROBACTER display and this is indicated by brackets around the F on the table. The B segment of the PROVIDENCIA display and the decimal point of the SHIGELL/YERSINIA display are also grounded in the minus test position of the ORNITHINE switch.

Each seven-segment display is turned on by a different AND gate. The AND gates are packaged three together in an integrated circuit. The integrated circuit receives 5 volts on pin 14 and is grounded on pin 7. If 5 VDC is supplied and pins 1, 2, and 13 are not grounded, pin 12 will supply a voltage to the associated seven-segment display. If pins 3, 4, and 5 are not grounded, pin 6 will supply a voltage to its associated display. The third gate similarily supplies a voltage to its associated display. The connections are indicated on the table. For example the ARIZONA display is connected to pin 6 of the AND gate integrated circuit 58 (the fifth AND gate chip), and pin 3 is connected to the positive side of the OXIDASE switch. Thus the table gives AND gate to LED as 5—6 for fifth chip, pin 6 and also gives OXIDASE as 5—3 for fifth chip, pin 3. Pin 4 of the fifth gate (gate 58) is connected to the positive side of the PHENYLALANINE switch and pin 5 of the fifth gate is connected to the UREASE switch, as also indicated by the table. In all cases given in table 1, the AND gate connection is to the positive side of the switches: the result is than when all switches are in the positive position, none of the segments will light because all of the AND gates will fail to supply voltage to the displays. If all switches are in the negative position (except GLUCOSE and NITRATE) eleven of the displays will have one or more segments lighted, and the SHIGELLA display will have all segments lighted. The GLUCOSE switch is labeled FERMENTS instead of positive and OXIDIZES instead of negative. When the GLUCOSE switch is in the negative position, 5 VDC goes directly to the second triple AND gate unit 52. Two of the AND gates in unit 52 are unused on models A, E, and M but not on models B and C, and pin 8 is connected to the PSEUDOMONAS display. Therefore, when the GLUCOSE switch is in the negative or OXIDIZES position and INDOLE, ORNITHINE, and SULFIDE switches are in the negative position the PSEUDOMONAS display will be turned on. If all of the 15 switches are in the negative position, only the PSEUDOMONAS display is lighted, and only segments E, G, F, and the decimal point show.

The GLUCOSE switch is connected when in the positive position to the NITRATE switch, which is connected when in the positive position to all of the AND gates except the second triple unit 52. In other words, when the GLUCOSE and NITRATE switches are in positive position, 5 VDC will be supplied to the first, third, fourth and fifth triple AND gate units 50, 54, 56 and 58.

When the GLUCOSE switch is in the positive position and the NITRATE switch is in the negative position, a lamp 60 lights. This lamp indicates that an unusual condition exists in that the test results do not indicate one of the 12 genera of bacteria. Alternate printed circuit boards may be developed whereby one or more of these boards may be used to replace the basic board and the unusual genus of bacteria may be identified. The nitrate switch is a double-pole double-throw (DPDT) switch and the second set of contacts of this switch operates like the thirteen basic switches. When it is in the positive position, it grounds the C segment of the PSEUDOMONAS display.

In Table 1, the notation X indicates that these is no connection. The notations # and # # for GLUCOSE and NITRATE indicate that the two switches are interconnected, and reference should be made to the drawing.

Table 2 adds a notation # # # , which indicates that GLUCOSE neither FERMENTS nor OXIDIZES. Therefore, the GLUCOSE switch must be left in a center position and another switch, possibly a push button, can be used in the embodiment of model B to supply 5 VDC directly to a sixth AND gate integrated circuit. The notation # # indicates that the second and seventh AND gate integrted circuits are supplied 5 VDC when the GLUCOSE switch is in the OXIDIZES position. The notation ⋆ indicates that the NITRATE switch is connected in the same way as in the models described in Tables 1, 3, 4, and 5. In the model of Table 2, certain AND gates have two or three pins connected to one switch. This is due to a present lack of sufficient information about those particular bacteria to make a better discrimination; the wiring can be changed if more is learned.

The fact that the AND gate are connected only to the positive side of the respective switches in the device of FIG. 1 is due to an arbitrary decision. In model C (table 3), for example, at least one of the three inputs to most AND gates is connected to the negative side of a switch. For example, 100% of the ARIZONA bacteria are positive for LYSINE, and, in Table 3, the LYSINE switch is indicated as having the negative side of that switch connected to circuit 5, pin 3. This is written 5+3 rather than 5—3 to indicate that distinction. Any test group with a negative LYSINE test would not turn on a segment of the ARIZONA display because the segment pin would be grounded.

In the invention, both positive and negative information is fed into the device, and the circuits rearrange these facts into a distinctive visual output. The displays are then easily interpreted to identify the genus (and in some cases, also the species) of bacteria. Even when one or more tests yield results which differ from the results expected in the majority of the strains of that genus of bacteria, identification will generally be possible and rapid.

The AND gates operate when five switches (four switches for PSEUDOMONAS) are in the correct position. That is, in 11 cases the AND gates operate when GLUCOSE and NITRATE are in the positive position and three other swtiches are in negative position (except in model C). These three other switches are selected to represent the most significant tests for the particular genus.

Each segment of the display has significance relative to the other segments. The A segment is most important and is operated by the most significant test (besides the tests which operate the AND gate) for that particular genus. The B segment is only slightly less important than and in some cases is of equal importance to the A segment. The C segment is less significant than the B segment but more significant than the D segment, etc. Therefore, tests which are exactly correct for a genus will light every segment of the display, including the decimal point (DP). If the least significant test is incorrect, the visual representation will be B instead of B followed by a decimal. A visual representation of O. means that the G segment is unlit and therefore the test is incorrect. If several displays have segments lit and the visual displays resemble: ⊓ ., O ., ᑫ ., U., L., E and H, then the genus indicated by the U with decimal is correctly identified but is a mutant bacterium which gives an incorrect test for the G segment. The ⊓ . has four incorrect tests, the U has only two incorrect tests but one of them is the A segment, etc. Learning to interpret the LED displays is easier than memorizing all of tests for each genus and their relative importance.

Model A (in FIG. 1 and Table 1) uses the most significant 13 of 15 tests (12 for PSEUDOMONAS) for each display. Therefore the two least significant tests have no effect on the visual representation. For exlample, ARABINOSE and RHAMNOSE are not used to identify EDWARDSIELLA because 9.3% of the members of EDWARDSIELLA are positive for ARABINOSE and RHAMNOSE is not even that consistent. The percent of positive or negative for the tests used for segments A down to the decimal point are: 0, 0, 100, 100, 0, 99.7, 99.1, 98.2. The argument might be made that the sequence should be: 100, 100, 99.7, 99.1, 98.2, 0, 0, 0, or 0, 0, 0, 100, 100, 99.7, 99.1, 98.2. However, choices of most significant, next most significant, etc., are based on a variety of factors other than the obvious mathematical consideration. There are pairs of bacterial genera such as ARIZONA and SALMONELLA which are closely related and therefore difficult to separate. Another such pair is ENTEROBACTER and KLEBSIELLA.

The species of bacteria can be determined in some cases. For example the correct tests for ENTEROBACTER will identify ENTEROBACTER aerogenes by giving a visual representation of B. An incorrect LYSINE test will leave the decimal unlit but this is the correct result for ENTEROBACTER cloacae. Incorrect RHAMNOSE and LACTOSE tests leave G and F segments unlit: correct for ENTEROBACTER liquifaciens and appears visually as ⊐ . ENTEROBACTER hafniae can be identified by an experienced operator when the LED shows a reversed E. (Ǝ.) In the same way various species of PROTEUS, PROVIDENCIA, PSEUDOMONAS, and other genera may be identified.

By using printed circuit boards and providing a few extra switches it will be possible to modify the original model to meet the needs of both large and small laboratories and to allow for the improvement of our understanding of significant differences between the genera of bacteria.

Model C uses both negative and positive tests to turn on the AND gates. This has the practical advantage of never allowing as many LED tubes to be turned on at one time as in the other models. The operator would therefore be somewhat faster in interpretation of the results. It also provides two displays for AEROMONAS and two displays for PSEUDOMONAS. This is because AEROMONAS and PSEUDOMONAS have species which are very different one from another.

FIG 5 discloses a modification using DPDT switches, one side of which serves the circuit of FIG. 5, and the other side of which serves the circuit of FIG. 1. Thus, when the seven-segment display does not light up completely, and indication of the percentage of bacteria of the most likely genera that have abnormal reactions can be provided. For example, about 20 % of the SHIGELLA give a positive ORNITHINE test. Such abnormal results would cause the decimal point to fail to light on the seven-segment display. The operator would observe the figure 8 without decimal, press the button labelled SWITCH NORMALLY OPEN on the figure, and various of the 32 LED lamps in FIG. 5 would light. If operator has already determined that the genus is probably SHIGELLA, he will look to the two LED lights labelled SHIGELLA and the one labelled 20% will indicate the probability. If there is any doubt about the genus being SHIGELLA, the only other choice would be SALMONELLA. The seven-segment display for SALMONELLA would have four unlit segments so the operator would look to the five lamps labelled SALMONELLA. Four of the five would be lit. These four would indicate 5.4, 5.4, 9.7, and 8.4%. Because none of these numbers is larger than 20%, the genus would be identified as most probably SHIGELLA.

Another example may clarify the problem better. consider the example results as follows: An unidentified bacterial culture is found to be positive for ARABINOSE, INDOLE, GLUCOSE, NITRATE, and RHAMNOSE, but negative for CITRATE, LACTOSE, LYSINE, MALONATE, MOTILITY, ORNITHINE, OXIDASE, PHENYLALANINE, SULFIDE, and UREA. The positive RHAMNOSE is not characteristic of SHIGELLA, but some of the bacteria in SHIGELLA in nature are RHAMNOSE positive. The negative LACTOSE and LYSINE tests are also not characteristic of ESCHERICHIA but a relative few of the ESCHERICHIA are negative for these tests. The operator observes that the seven segment display shows Ɔ. for ESCHERICHIA and a figure 8 without decimal for SHIGELLA. A few segments of some other seven-segment displays are lighted, but the choice is obviously between ESCHERICHIA and SHIGELLA. The operator pushes the pushbotton to light the single LED lights and observes the lights for ESCHERICHIA and SHIGELLA. For SHIGELLA only the light labelled 16.6% is lit. For ESCHERICHIA only the lights labelled 9.2% and 11.3% are lit. The genus is SHIGELLA because 16.6% of the SHIGELLA are able to give the combination of tests and only about 1% (11.3 times 9.2) of the ESCHERICHIA give the combination. The 1% is an estimate and might be much in error but could not be as large as 9%. Therefore the identification of the unknown would be correct usually if it were called a SHIGELLA. The laws of probability should tell us that in some cases the unknown would still be identified incorrectly (in one case out of 17 in this case).

TABLE 1

FOR MODEL A

| | AND gate to LED | Ara-bi-nose | Ci-trate | Glu-cose (FERM/OXID) | In-dole | Lac-tose | Ly-sine | Malo-nate | Mo-til-ity | Ni-trate | Or-nith-ine | Oxi-dase | Phenyl-ala-nine | Rham-nose | Sul-fide | Ur-ease |
|---|---|---|---|---|---|---|---|---|---|---|---|---|---|---|---|---|
| Arizona | 5–6 | DP | E | 〃 | (F) | X | B | G | C | 〃 | A | 5–3 | 5–4 | X | D | 5–5 |
| Citrobacter | 5–8 | A | E | 〃 | (D) | X | 5–9 | (G) | C | 〃 | (F) | 5–10 | 5–11 | B | X | DP |
| Edwardsiella | 5–12 | X | 5–1 | 〃 | G | 5–2 | C | 5–13 | DP | 〃 | D | (A) | (B) | X | F | (E) |
| Enterobacter | 4–6 | C | E | 〃 | 4–3 | F | DP | X | D | 〃 | B | 4–4 | (A) | G | 4–5 | X |
| Escherichia | 4–8 | D | (C) | 〃 | E | F | G | (B) | X | 〃 | X | (A) | 4–9 | DP | 4–10 | 4–11 |
| Klebsiella | 3–6 | C | F | 〃 | (DP) | E | G | X | 3–3 | 〃 | 3–4 | (A) | (B) | D | 3–5 | X |
| Proteus | 3–8 | 3–9 | X | 〃 | F | (C) | 3–10 | (B) | E | 〃 | G | 3–11 | A | X | DP | D |
| Providencia | 3–12 | (G) | DP | 〃 | C | (F) | (A) | (D) | X | 〃 | (B) | X | E | 3–1 | 3–2 | 3–13 |
| Pseudomonas | 2–8 | X | D | 〃〃 | 2–9 | (E) | (F) | X | A | C | 2–10 | B | X | (G) | 2–11 | (DP) |
| Salmonella | 1–6 | X | X | 〃 | (C) | (B) | E | (A) | D | 〃 | F | 1–3 | 1–4 | DP | G | 1–5 |
| Serratia | 1–8 | 1–9 | E | 〃 | (B) | (DP) | C | (G) | F | 〃 | D | (A) | X | 1–10 | 1–11 | X |
| Shigella/Yersinia | 1–12 | X | 1–1 | 〃 | X | (F) | 1–2 | (C) | 1–13 | 〃 | (DP) | (A) | (B) | (G) | (D) | (E) |

TABLE 2

FOR MODEL B

| | AND gate LED | AND gate to LED | Ara-bi-nose | Ci-trate | Glu-cose (FERM/OXID) | In-dole | Ly-sine | Mo-til-ity | Ni-trate | Or-nith-ine | Oxi-dase | Phenyl-ala-nine | Rham-nose | Sul-fide | U-re-ase |
|---|---|---|---|---|---|---|---|---|---|---|---|---|---|---|---|
| Achromobacter | R | 7–6 | | D | 〃〃 | 7–3 7–4 7–5 | | C | B | | A | | | | (E) |
| Acinetobacter | Q | 7–8 | | | 〃〃 | (A) | 7–9 | 7–10 | | 7–11 | | | | | |
| Aeromonas | P | 4–12 | | | 〃 | D | C | B | | A | | | 4–1 | | 4–2 4–13 |
| Alcaligenes/Bord. | O | 6–6 | | E | 〃〃〃 | 6–3 6–4 6–5 | | D | C | | A | | | | B |
| Arizona | N | 5–6 | F | D | 〃 | (G) | B | C | 干 | A | 5–3 | 5–4 | DP | E | 5–5 |
| Citrobacter | M | 5–8 | A | E | 〃 | (D) | 5–9 | C | 干 | (F) | 5–10 | 5–11 | B | G | DP |
| Edwardsiella | L | 5–12 | DP | 5–1 | 〃 | E | B | G | 干 | C | 5–2 | (A) | 5–13 | D | (F) |
| Enterobacter | K | 4–6 | C | E | 〃 | 4–3 | F | D | 干 | B | 4–4 | (A) | G | 4–5 | DP |
| Escherichia | J | 4–8 | C | (B) | 〃 | D | E | G | 干 | DP | (A) | 4–9 | F | 4–10 | 4–11 |
| Klebsiella | I | 3–6 | C | E | 〃 | (DP) | F | 3–3 | 干 | 3–4 | (A) | (B) | D | 3–5 | G |
| Moraxella | H | 6–8 | | 6–9 | 〃〃〃 | 6–10 | | 6–11 | (C) | | A | | | | (B) |
| Proteus | G | 3–8 | 3–9 | DP | 〃 | D | 3–10 | C | 干 | E | 3–11 | A | (G) | F | B |
| Providencia | F | 3–12 | (E) | F | 〃 | D | 3–1 | DP | 干 | (C) | (A) | G | (B) | 3–2 | 3–13 |
| Pseudomonas 1 | E | 2–6 | | B | 〃〃 | 2–3 | (C) | E | D | 2–4 | A | | G | 2–5 | (F) |
| Pseudomonas 2 | D | 2–8 | | (G) | 〃〃 | 2–9 | B | A | 2–10 | (C) | 2–11 | | (F) | (E) | (D) |
| Salmonella | C | 1–6 | DP | G | 〃 | (A) | C | B | 干 | D | 1–3 | 1–4 | F | E | 1–5 |
| Serratia | B | 1–8 | 1–9 | E | 〃 | (B) | C | F | 干 | D | (A) | (G) | 1–10 | 1–11 | (DP) |
| Shigella/Yersinia | A | 1–12 | G | (D) | 〃 | (DP) | 1–1 | (A) | 干 | (F) | 1–2 | 1–13 | (E) | (B) | (C) |

TABLE 3

FOR MODEL C

| | AND gate to LED | Arabinose | Citrate | Dulcitol | Glucose (Ferment/Oxidize) | Indole | Lysine | Malonate | Motility | Nitrate | Ornithine | Oxidase | Phenylalanine | Rhamnose | Sulfide | Urea |
|---|---|---|---|---|---|---|---|---|---|---|---|---|---|---|---|---|
| Aeromonas 1 | 6–6 | DP | G | (C) | ⌗ | E | (B) | X | A | ⌗ | 6–3 | 6+4 | X | (F) | 6–5 | (D) |
| Aeromonas 2 | 6–8 | (DP) | (D) | (F) | ⌗ | G | A | X | X | ⌗ | B | 6+9 | 6–10 | (E) | 6–11 | C |
| Arizona | 5–6 | DP | E | (D) | ⌗ | (G) | 5+3 | DP | C | ⌗ | B | (A) | 5–4 | X | F | 5–5 |
| Citrobacter | 5–8 | 5+9 | E | X | ⌗ | (D) | 5–10 | X | C | ⌗ | (G) | (A) | 5–11 | B | F | DP |
| Edwardsiella | 5–12 | X | 5–1 | (F) | ⌗ | G | C | X | E | ⌗ | 5+2 | (A) | (B) | 5–13 | D | (DP) |
| Enterobacter | 4–6 | C | F | (D) | ⌗ | 4–3 | DP | X | E | ⌗ | B | 4–4 | (A) | G | 4–5 | X |
| Escherichia | 4–8 | E | (B) | X | ⌗ | C | F | (D) | DP | ⌗ | X | (A) | 4–9 | G | 4–10 | 4–11 |
| Klebsiella | 3–5 | 3+3 | D | X | ⌗ | (F) | G | X | 3–4 | ⌗ | 3–5 | (A) | (B) | DP | (C) | E |
| Proteus | 3–8 | 3–9 | X | (D) | ⌗ | F | 3–10 | (E) | C | ⌗ | G | 3–11 | A | X | DP | B |
| Providencia | 3–12 | X | G | (D) | ⌗ | F | 3–1 | X | DP | ⌗ | (B) | (A) | E | (C) | 3–2 | 3–13 |
| Pseudomonas 1 | 2–6 | X | B | DP | ⌗⌗ | 2–3 | (C) | X | E | D | 2–4 | A | X | (G) | 2–5 | (F) |
| Pseudomonas 2 | 2–8 | X | (G) | DP | ⌗⌗ | 2–9 | B | X | A | 2–10 | (C) | 2–11 | X | (F) | (E) | (D) |
| Salmonella | 1–6 | X | X | E | ⌗ | (B) | C | (A) | G | ⌗ | D | 1–3 | 1–4 | DP | F | 1–5 |
| Serratia | 1–8 | 1–9 | G | X | ⌗ | (C) | 1+10 | (E) | F | ⌗ | D | (A) | (DP) | 1–11 | (B) | X |
| Shigella/Yersinia | 1–12 | X | (D) | (F) | ⌗ | X | 1–1 | (E) | 1–2 | ⌗ | (DP) | (A) | 1–3 | (G) | (B) | (C) |

TABLE 4

FOR MODEL E

| | AND gate to LED | Citrate | Dulcitol | Gas | Glucose (Ferment/Oxidize) | Indole | Lactose | Lysine | Ornithine | Oxidase | Phenylalanine | Sulfide | Urease |
|---|---|---|---|---|---|---|---|---|---|---|---|---|---|
| Arizona | 5–6 | F | 5–3 | D | ⌗ | (G) | DP | C | B | (A) | 5–4 | E | 5–5 |
| Citrobacter | 5–8 | C | G | B | ⌗ | (A) | (DP) | 5–9 | (D) | 5–11 | 5–10 | E | F |
| Edwardsiella | 5–12 | 5–1 | 5–2 | G | ⌗ | DP | (B) | E | D | (A) | 5–13 | F | (C) |
| Enterobacter | 4–6 | E | (D) | B | ⌗ | 4–4 | F | G | C | 4–3 | (A) | 4–5 | (DP) |
| Escherichia | 4–8 | (B) | (DP) | D | ⌗ | C | E | F | G | 4–9 | 4–10 | (A) | 4–11 |
| Klebsiella | 3–6 | C | (DP) | E | ⌗ | (G) | B | D | 3–4 | 3–3 | (A) | 3–3 | F |
| Proteus | 3–8 | (DP) | 3–11 | E | ⌗ | D | (B) | 3–9 | F | 3–10 | A | G | C |
| Providencia | 3–12 | E | 3–1 | (G) | ⌗ | C | (D) | (A) | (B) | (DP) | F | 3–2 | 3–13 |
| Pseudomonas | 2–8 | E | DP | (G) | ⌗⌗ | 2–9 | (B) | (C) | 2–10 | A | F | 2–11 | (D) |
| Salmonella | 1–6 | DP | G | E | ⌗ | (B) | (A) | C | D | 1–3 | 1–4 | F | 1–5 |
| Serratia | 1–8 | E | (A) | DP | ⌗ | 1–9 | (D) | B | C | 1–11 | (F) | 1–10 | (G) |
| Shigella/Yersinia | 1–12 | 1–1 | (F) | (E) | ⌗ | (DP) | (D) | 1–2 | (G) | (A) | 1–13 | (B) | (C) |

TABLE 5

FOR MODEL M

| | AND gate to LED | Arabinose | Citrate | Glucose (Ferment/Oxidize) | Indole | Inositol | Lactose (ONPG) | Lysine | Nitrate | Ornithine | Oxidase | Phenylalanine | Rhamnose | Sulfide | Urease |
|---|---|---|---|---|---|---|---|---|---|---|---|---|---|---|---|
| Arizona | 5–6 | F | E | ⌗ | (G) | 5–3 | X | C | ⌗ | B | (A) | 5–4 | DP | D | 5–5 |
| Citrobacter | 5–8 | A | E | ⌗ | (D) | (C) | X | 5–9 | ⌗ | (F) | 5–10 | 5–11 | B | G | DP |
| Edwardsiella | 5–12 | X | 5–1 | ⌗ | E | 5–2 | 5–13 | C | ⌗ | B | (A) | (F) | (D) | G | (DP) |
| Enterobacter | 4–6 | C | D | ⌗ | 4–3 | DP | G | F | ⌗ | B | 4–4 | (A) | E | 4–5 | X |
| Escherichia | 4–8 | C | (B) | ⌗ | E | (D) | F | G | ⌗ | X | (A) | 4–9 | DP | 4–10 | 4–11 |
| Klebsiella | 3–6 | B | F | ⌗ | X | E | D | G | ⌗ | 3–3 | (A) | 3–4 | C | 3–5 | DP |

TABLE 5-continued

| | FOR MODEL M | | | | | | | | | | | | | |
|---|---|---|---|---|---|---|---|---|---|---|---|---|---|---|
| | AND gate to LED | Arabinose | Citrate | Glucose (Ferment/Oxidize) | Indole | Inositol | Lactose (ONPG) | Lysine | Nitrate | Ornithine | Oxidase | Phenylalanine | Rhamnose | Sulfide | Urease |
| Proteus | 3–8 | 3–9 | X | ⌗ | D | (E) | (B) | 3–10 | ⌗ | G | 3–11 | A | (F) | DP | C |
| Providencia | 3–12 | (E) | F | ⌗ | B | DP | (D) | 3–1 | ⌗ | (C) | X | G | 3–2 | (A) | 3–13 |
| Pseudomonas | 2–8 | DP | C | ⌗⌗ | 2–9 | X | (B) | (F) | D | 2–10 | A | X | (G) | 2–11 | (E) |
| Salmonella | 1–6 | G | DP | ⌗ | (B) | X | (A) | C | ⌗ | D | 1–3 | 1–4 | F | E | 1–5 |
| Serratia | 1–8 | 1–9 | E | ⌗ | (B) | DP | (F) | C | ⌗ | D | (A) | (G) | 1–10 | 1–11 | X |
| Shigella/Yersinia | 1–12 | DP | 1–1 | ⌗ | X | (D) | (B) | 1–2 | ⌗ | (G) | 1–13 | (C) | (F) | (A) | (E) |

What is claimed is:

1. A device for evaluating a first plurality of test results obtained by testing a test sample to determine into which of a second plurality of categories the test sample should be classified, comprising:
   A. a first plurality of manually operated electrical switch means for entering the first plurality of test results into the device as switch positions,
   B. a second plurality of sets of lamps, each set of lamps corresponding to a respective one of the second plurality of categories,
   C. first logic means responsive to the respective switch positions for controlling the lighting of individual lamps in respective sets of lamps for which the results of the respective test corresponding to the respective switch has a significant positive correlation with the respective category corresponding to the respective set of lamps, and
   D. second logic means responsive to the respective switch positions and operative to enable or disable the lighting of all of the lamps in respective sets of lamps,
      whereby a given lamp is lighted if and only if the second logic means causes the set of lamps containing the given lamp to be enabled to be lighted and the first logic means causes the given lamp within an enabled set to be lighted.

2. A device for evaluating results of a plurality of biological tests conducted on a sample of bacteria of unknown type to determine which of a number of categories of bacteria types contains the unknown type of bacteria, comprising:
   A. a number of multi-segment numerical display elements corresponding respectively to the number of categories, each display comprising one common electrode and an opposite polarity electrode corresponding to each segment, each element representing one of the categories,
   B. a plurality of electrical switch means corresponding respectively to the plurality of biological tests, each switch means providing means for entering and storing the results of one of the tests,
   C. a number of logic gates corresponding respectively to the number of display elements, each gate having an output terminal connected to a common electrode of a respective display element for providing a gate output signal to enable or not enable operation of the respective display element, each gate having a plurality of input terminals for jointly controlling the signal applied to the common electrode, each plurality of input terminals being connected to a corresponding selected number of the plurality of switch means, said corresponding number of switch means being selected from among those switch means corresponding to the most significant tests, whereby the most significant selected tests control the enabling of the common electrode, and
   D. means for connecting a second number of the plurality of switch means to corresponding opposite polarity electrodes of each display element, said second number of switch means being next most significant after said selected number of switch means in corresponding to the most significant tests, whereby each of the second number of switch means operates to control the lighting of one segment of the corresponding display element if that element is enabled at the common electrode by the corresponding gate.

3. A device according to claim 2 further comprising:
   A. an additional lamp for indicating abnormal readings,
   B. two additional switch means for entering and storing the results of two additional biological tests,
   C. first means operative when a first of the two additional switches is in a first position for enabling operation of at least one of the logic gates,
   D. second means operative when the first additional switch is in a second position and when the second of the two additional switches is in a first position for enabling operation of the logic gates which are not enabled by the first means, and
   E. means operative when the first additional switch is in the second position and when the second additional switch is in a second position for lighting the additional lamp.

4. A device for evaluating a first plurality of test results obtained by testing a test sample to determine into which of a second plurality of categories the test sample should be classified, comprising:
   A. a first plurality of manually operated electrical switch means for entering the first plurality of test results into the device as switch positions,
   B. a second plurality of sets of lamps, each set of lamps corresponding to a respective one of the second plurality of categories, and
   C. logic means responsive to the respective switch positions for controlling the lighting of individual lamps in respective sets of lamps for which the results of the respective test corresponding to the respective switch has a significant positive correlation with the respective category corresponding to the respective set of lamps,
   wherein each set of lamps is embodied in a numerical display element comprising a set of light-emitting diodes, each diode comprising one segment of the numerical display element.

* * * * *